US008663688B2

(12) United States Patent
Acebrón Fernández et al.

(10) Patent No.: US 8,663,688 B2
(45) Date of Patent: Mar. 4, 2014

(54) SEMI-SOLID MUCOADHESIVE FORMULATIONS

(75) Inventors: Álvaro Acebrón Fernández, Alcobendas (ES); Ana Campuzano Garcia, Alcobendas (ES); Rosa Maria Hernández Martin, Vitoria-Gasteiz (ES); Manuela Igatúa Olaechea, Vitoria-Gasteiz (ES); José Luis Pedraz Muñoz, Vitoria-Gasteiz (ES); Alicia Rodriguez Gascón, Vitoria-Gasteiz (ES)

(73) Assignee: ITF Research Pharma, S.L.U., Madrid (ES)

( * ) Notice: Subject to any disclaimer, the term of this patent is extended or adjusted under 35 U.S.C. 154(b) by 1640 days.

(21) Appl. No.: 10/565,062

(22) PCT Filed: Jul. 16, 2004

(86) PCT No.: PCT/ES2004/000336
§ 371 (c)(1),
(2), (4) Date: Jun. 15, 2006

(87) PCT Pub. No.: WO2005/007194
PCT Pub. Date: Jan. 27, 2005

(65) Prior Publication Data
US 2006/0240111 A1    Oct. 26, 2006

(30) Foreign Application Priority Data
Jul. 16, 2003   (ES) .................................. 200301672

(51) Int. Cl.
*A61K 9/14* (2006.01)

(52) U.S. Cl.
USPC .......................... 424/487; 424/486; 424/484

(58) Field of Classification Search
USPC ........................................................ 424/487
See application file for complete search history.

(56) References Cited

U.S. PATENT DOCUMENTS

| 5,719,197 | A | * | 2/1998 | Kanios et al. ............. 514/772.6 |
| 5,942,243 | A |   | 8/1999 | Shah |
| 6,967,194 | B1 | * | 11/2005 | Matsuo et al. ................ 514/171 |
| 2003/0022877 | A1 | * | 1/2003 | Dudley ........................ 514/177 |

FOREIGN PATENT DOCUMENTS

| EP | 0431719 | 11/1994 |
| EP | 0719146 | 12/1998 |
| EP | 0500807 | 7/1999 |
| EP | 0818194 | 1/2002 |
| EP | 1325752 | 7/2003 |
| ES | 2173203 | 7/1997 |
| GB | 2199495 | 7/1988 |
| WO | 8502092 | 5/1985 |
| WO | 9507699 | 3/1995 |
| WO | 9610989 | 4/1996 |
| WO | 9629056 | 9/1996 |
| WO | 9715314 | 5/1997 |
| WO | 9805303 | 2/1998 |
| WO | 9820872 | 5/1998 |
| WO | 9913862 | 3/1999 |
| WO | 0047144 | 8/2000 |
| WO | 0050078 | 8/2000 |
| WO | 0124788 | 4/2001 |
| WO | WO 01/28155 | 4/2001 |
| WO | WO 03/037382 | 5/2003 |
| WO | WO 2005/007194 A1 | 1/2005 |

OTHER PUBLICATIONS

Senel et al.; "Controlled Release of Biactive Materials"; 28th International Symposium—Idrugs; 2001; pp. 1008-1009; vol. 4.
Kockisch et al.; "A Direct-staining Method to Evaluate the Mucoadhesion of Polymers from Aqueous Dispersion"; Journal of Controlled Release; 2001; pp. 1-6; vol. 77.
Peh et al.; "Polymeric Films as Vehicle for Buccal Delivery: Swelling, Mechanical, and Bioadhesive Properties"; J. Pharm Pharmaceut Sci (www.ualberta.ca/-csps); 1999; pp. 53-61; vol. 2, No. 2.
Chang et al.; "Rheological Evaluation of Thermosensitive and Mucoadhesive Vaginal Gels in Physiological Conditions"; International Journal of Pharmaceutics; 2002; pp. 155-163; vol. 241.
Pinkerton et al.; "Alternatives to the Use of Estrogen in Postmenopausal Women"; Endocrine Reviews, downloaded from edrv.endojournals.org; Apr. 30, 2008; pp. 308-320; vol. 20, No. 3.

* cited by examiner

*Primary Examiner* — James Rogers
(74) *Attorney, Agent, or Firm* — Thompson Coburn LLP (57) ABSTRACT

Semisolid mucoadhesive formulations for vaginal application, with improved technical and organoleptic characteristics, which contain at least two bioadhesive gelling polymers and an active ingredient, useful in the prevention and/or treatment of various pathologies and disorders in human beings or animals.

22 Claims, 3 Drawing Sheets

SEMI-SOLID MUCOADHESIVE FORMULATIONS

This invention relates to semisolid mucoadhesive formulations for vaginal application, which comprise at least two bioadhesive gelling polymers and an active ingredient. It also relates to processes to prepare them and to their uses in the prevention or treatment of various pathologies and disorders of human beings or animals.

STATE OF THE ART

The term bioadhesion is used to define the ability of a natural or synthetic material to adhere to biological membranes, resulting in intimate contact of the material with the tissue for a more or less prolonged period of time. Mucoadhesion relates to a special case of bioadhesion wherein the tissue is a mucous membrane.

These concepts have received a significant amount of attention due to their potential application in drug administration. Although there is a debate regarding the bioadhesion mechanism, most researchers agree that this phenomenon is of interest as it increases the residence time of a pharmaceutical form at the absorption site, and this may result in an increase in drug bioavailability.

A controlled-release bioadhesive formulation can improve the efficacy and/or safety of a treatment helping to maintain the drug concentrations between the effective and toxic levels, being located in a specific tissue, increasing the intimateness and duration of contact between the drug-polymer complex and the tissue surface.

Furthermore, when a bioadhesive composition is administered topically (e.g. vaginally) it does not undergo first-pass metabolism through the liver.

Bioadhesive pharmaceutical products can be presented in different forms (particles, suspensions, tablets, suppositories, gels, etc.) and be administered by different routes (ocular, nasal, vaginal, gastrointestinal, rectal, dermal, etc.).

The administration of drugs by vaginal route can be a preferred alterative in certain cases although, for the treatment to be successful, some difficulties must be overcome.

The formulations to be used by this route should be carefully designed in order to not produce side effects in the patient that lead to the treatment not be concluded. It has been seen that tablets and suppositories may cause discomfort (irritation), ovules and creams may cause excessive vaginal flow.

Furthermore, it is preferable that the compositions have good bioadhesive properties as, due to the vagina's anatomic and physiological characteristics, it is very difficult to achieve that they remain adhered to its walls and can release the drug in this area for a prolonged period of time.

Documents EP 0431719, EP 0500807, EP 0719146, WO 96/10989, WO 99/13862 and WO 01/24788 disclose bioadhesive formulations with a crosslinked carboxylic acid polymer (Polycarbophil) and a gelling polymer (preferably Carbopol 934P) which may contain different active ingredients.

Documents FR 2609391 and GB 2199495 disclose bioadhesive suppositories for vaginal application formed from, at least, one hydrophilic polymer (NaCMC, HPMC or Carbopol) and a drug (antifungals of nystatin or imidazole type).

Document WO 85/02092 discloses bioadhesive compositions for application on skin or mucous membranes which include a crosslinked carboxy-functional polymer (Polycarbophil) and a therapeutic agent.

Document U.S. Pat. No. 5,942,243 discloses a mucoadhesive composition in the form of hydrogel which comprises one or more drugs (clotrimazole, nonoxynol-9, progesterone, etc.) and a thermoplastic copolymer.

Document EP 0818194 discloses biomembrane-adhesive hydrating compositions which preferably comprise a polymer crosslinked with carboxyl groups (Stablese, Carbopol 934P), a water-soluble polymer (Gantrez, NaCMC) and a polyhydroxylated compound (glycerine, propylene glycol). They may optionally contain drugs (antifungal agents, antibacterial agents, antivirals, spermicides, etc.).

Document WO 97/15314 discloses a vaginal pharmaceutical composition in the form of a gel which contains a source of peroxide (hydrogen peroxide), a buffer system (citric acid/citrate), a water-soluble bioadhesive polymer (Carbopol 974P) and, optionally, an additional therapeutic agent (nonoxynol-9, etc.).

Document WO 98/20872 discloses topical formulations which comprise a microbicide lipid (monocarpin) in a hydrogel-forming agent (Carbopol, povidone, NaCMC, etc.).

Document WO 98/05303 discloses mucoadhesive complexes of Polycarbophil and antifungals or antiprotozoals (of imidazole or triazole-type) useful in the topical treatment of mucous membrane diseases, and gel formulations that contain them.

Document WO 00/47144 discloses a vaginal bioadhesive composition based on a synergic formula of carrageenin, agarose, acrylic acid polymers (Pemulen) or Polycarbophil and therapeutic agent.

Document WO 00/50078 discloses microspheres for application on mucous membranes which comprise at least one antigen and a bioadhesive (HPMC, Carbopol, Polycarbophil).

In short, many bioadhesive pharmaceutical formulations have been studied in recent years, not always with success. There, therefore, exists the need for new compositions with optimized bioadhesive and organoleptic properties, in particular for vaginal application.

The vagina is a hollow fibromuscular tube formed from three tissue layers: mucous, muscular and adventitia.

Vaginal mucous is formed by stratified non-keratinized squamous epithelium, lacking glands.

The vaginal epithelium is sensitive to hormones and shows cyclical and age-dependent changes, both morphological and functional. A physical atrophy occurs until puberty. During puberty, by action of ovarian hormones, the epithelium increases its thickness and resistance to begin to be more or less atrophic once the menopause starts.

Vaginal mucous continues towards the exterior, in the external genitals, forming vulvar mucous, comprised of an epithelium similar to that of the vaginal epithelium.

The vagina is colonized by mixed bacterial flora wherein lactobacillus dominate. Up to the menopause, the normal pH is between 3.5 and 4.5. In post-menopausal women, the vaginal pH becomes relatively high and it loses the lactobacillus colonies.

The physiological functionality of the vulvovaginal area may facilitate, in certain circumstances, that inflammatory or infectious pathologies take hold.

Inflammatory conditions which affect the vaginal mucous, and may also affect the vulva, are called vulvovaginitis. They may be secondary to multiple causes including infections, irritation, allergy or systemic diseases.

For the symptomatic release of extreme vaginal pruritus, especially in paediatric vulvovaginitis, the topical administration of adrenocorticoids is usually resorted to (on skin or external mucous membranes).

Vulvovaginal infections require treatment with different drugs by oral or intravaginal route, e.g. antiseptics, antibiotics, antimycotics or antivirals, depending on their etiology.

Atrophic vulvovaginitis is usually treated with topical hydrating gels (vaginal), without active ingredient or with estrogens, depending on their cause.

There also exist other indications for treatment by vaginal route, both to tackle local problems and systemic disorders.

The difficulty or impossibility of conceiving or maintaining pregnancy may require stimulation/support of the luteum phase in women of fertile age.

Likewise, in repeated miscarriages or threats of miscarriage, the empirical administration of natural progesterone by vaginal route is used.

Hormone administration is typically used in assisted reproduction programs (by different techniques), preferably natural progesterone, both by oral and vaginal route. Estriol is also administered by vaginal route in some of these programs.

For labour induction or finalization of gestation, prostaglandins or their analogues are administered, with a view to the maturation and dilatation of the uterine cervix and uterine stimulation.

In cicatricial pathologies, for example after an episiotomy postpartum or after cervical conization, drugs which favour healing are usually administered topically.

Furthermore, given the necessity of contraceptive methods, the administration of gestagens and estrogens by vaginal route has been proposed.

SUMMARY OF THE INVENTION

There, therefore, exists the need for easily-applied vaginal mucoadhesive pharmaceutical compositions, high bioadhesion capacity, non-irritant or uncomfortable for the patient and which permit the release of active ingredients in accordance with the preventive and/or therapeutic objectives desired.

The inventors of the present invention have found that the combination of at least one first bioadhesive gelling polymer of polyacrylic acid type crosslinked with divinyl glycol and at least one second bioadhesive gelling polymer derived from acrylic acid crosslinked with allyl sucrose or allyl pentaerythritol allows semisolid formulations with good bioadhesive capacity to be obtained. In other words, it enables prolonged direct contact of a pharmacologically active agent with biomembranes, ensuring an optimum action thereon without producing greater discomfort to the patient.

This combination of polymers also means that the resulting formulations are hydrating and have pleasant organoleptic properties which, together with their high bioadhesion, contribute to improving the conclusion of preventive or therapeutic treatments.

In consequence, a first aspect of the present invention relates to semisolid mucoadhesive formulations which comprise at least:
- a first bioadhesive gelling polymer of polyacrylic acid type crosslinked with divinyl glycol in a quantity between 0.1% and 5% by weight of the formulation,
- a second bioadhesive gelling polymer derived from acrylic acid crosslinked with allyl sucrose or allyl pentaerythritol, in a quantity between 0.1% and 5% by weight of the formulation,
- a hydrating/wetting agent in a quantity between 0% and 20% by weight of the formulation,
- a fat/lipophilic component, in a quantity between 0% and 50% by weight of the formulation,
- a solubilizing/emulsifying agent in a quantity between 0% and 70% by weight of the formulation,
- neutralizing agent in sufficient quantity to position the formulation's pH between 2 and 6,
- a pharmacologically active agent,
- water, in sufficient quantity to complete the formulation.

Furthermore, the combination of polymers of the present invention means the resulting mucoadhesive gels show great versatility. Thus, they can incorporate very different quantities of drugs (from hundredths to tenths of grams of active ingredient/100 grams of formulation) maintaining excellent bioadhesion and achieving prophylactic or therapeutic efficacy.

Likewise, the qualitative and quantitative selection of the components of the mucoadhesive formulations of the present invention, permits adjusting the transfer profile of the drug to the prophylactic and/or therapeutic objective sought in each case, making it possible to space out the applications (to one application daily or even more) and/or obtain a safe product.

In short, the formulations of the present invention can be easily applied by vaginal route, they have good bioadhesive capacity, they do not cause the patient irritation or discomfort, they have hydrating properties and permit the controlled release of the pharmacologically active agent in accordance with the desired profile for each clinical condition.

Another aspect of the present invention relates to processes for the preparation of the mucoadhesive formulations of the present invention.

Another aspect of the present invention relates to the use of the mucoadhesive gels of the present invention in the preparation of drugs for the prevention or treatment of various vaginal pathologies and disorders.

DETAILED DESCRIPTION OF THE INVENTION

A preferred class of bioadhesive gelling polymers to be used in this invention is that comprised of acrylic acid polymers crosslinked with allyl sucrose or allyl ethers of pentaerythritol, commercially available with the name Carbopol® (Carbomer) from B.F. Goodrich Chemical Co.

Carbopol® 934P is usually considered the ideal candidate for vaginal administration. During the development of the formulations of the present invention, it has surprisingly been found that other polymers, e.g. Carbopol® 971P, may be used with very good results.

Another preferred class of bioadhesive gelling polymer to be used in the present invention is that comprised of acrylic acid polymers crosslinked with divinyl glycol, commercially available with the trademark Noveon® AA-1 Polycarbophil USP (Polycarbophil AA1).

In particular, the combination of Carbopol® 971P NF and Polycarbophil AA1 gives excellent bioadhesive properties to the present formulations.

An embodiment of the present invention relates to semi-solid mucoadhesive formulations which comprise at least:
- a first bioadhesive gelling polymer of polyacrylic acid type crosslinked with divinyl glycol, in particular Polycarbophil AA1, in a quantity between 0.1% and 5% by weight of the formulation,
  - a second bioadhesive gelling polymer derived from acrylic acid crosslinked with allyl sucrose or allyl pentaerythritol, in particular Carbopol 971P, in a quantity between 0.1% and 5% by weight of the formulation,
  - a hydrating/wetting agent selected from the group formed by glycerine, propylene glycol, dipropylene glycol, polyethylene glycols (e.g. PEG-4, PEG-6, PEG-8), polyglycerols (such as diglycerol or triglycerol), sorbitol, pentaerythritol, methyl glucose ether derivatives, in a quantity between 0% and 20% by weight of the formulation,
- a fat/lipophilic component, selected from the group formed by paraffin, vaseline, mineral oil, vegetable oils (e.g. palm, corn, peanut), hydrogenated vegetable oils, in a quantity between 0% and 50% by weight of the formulation,
- a solubilizing/emulsifying agent selected from the group formed by fatty acid esters of polyethylene glycol (such as Labrafil M 1944), polyoxyethelenated derivatives of castor oil (such as Cremophor EL), phospholipids and their mixtures (such as egg lecithin, soya lecithin, etc.), fatty acid esters of polyoxyethylene sorbitan (e.g. Polysorbates 60 and 80), sodium alkyl sulphates (such as sodium lauryl sulphate), sorbitan esters, glyceryl monostearate, polyoxyethylene alkyl ethers, polyoxyethylene stearates in a quantity between 0% and 70% by weight of the formulation,
- a neutralizing agent, selected from the group formed by aqueous solutions of NaOH, KOH and triethanolamine, in sufficient quantity to position the formulation's pH between 2 and 6,
- a pharmacologically active agent,
- water, in sufficient quantity to complete the formulation.

In a more preferred embodiment Polycarbophil AA1 is used in a quantity between 0.5% and 2.5%, and more preferably between 0.75% and 1.5%, whilst Carbopol 971P is used in a quantity between 0.1% and 1%, and more preferably between 0.25% and 0.5% by weight of the formulation.

When the formulations of the present invention contain a hydrating agent, this will preferably be in a quantity between 5% and 15% by weight of the formulation.

When they include a fat and/or solubilizing component, this will preferably be in a quantity between 5% and 50%, and more preferably between 10% and 40% by weight of the formulation.

If it is also necessary to include an emulsifying agent, this will preferably be in a quantity between 0.1% and 15% by weight of the formulation.

In addition to the aforementioned components, the formulations of the present invention may also include other pharmaceutically acceptable additives.

Usual additives include preservative agents selected from parabens and their salts (e.g. methylparaben, propylparaben), sorbic acid and its salts, benzoic acid and its salts, etc., in a quantity between 0.02% and 1% by weight of the formulation.

Other additives which may be used are pH adjusters, flavourings, colouring agents and penetration enhancers.

The pH adjusters include acidifying agents selected from aqueous solutions of HCl, lactic acid and acetic acid.

The pharmacologically active agents that may be administered using the formulations of the present invention, but without being excessively limited to them, include: hormones, antibacterials, antifungals, antivirals, active agents against sexually transmitted diseases (anti-STD), spermicides, local anaesthetics, anti-inflammatories, smooth muscle relaxants (antispasmodics), labour inducers (prostaglandins), etc.

By way of non-limiting example, we can cite the following:

Estrogens: estriol, 17-β-estradiol.

Progestagens: progesterone, medrogestone, medroxyprogesterone.

Antiprotozoals: metronidazole.

Antibacterials: clindamycin, trimetoprim, sulfamethoxazole, penicillins (ampicillin, methicillin), cepholosporins, tetracyclines (doxycyclin), bacitracin, lincomycin, colistin, polymyxin B, vancomycin, gentamicin, kanamycin, neomycin, treptomycin, erythromycin, amikacin, tobramycin.

Antifungals: clotrimazole, ketoconazole, miconazole, fenticonazole, tioconazole, sertaconazole, oxiconazole, itraconazole, butaconazole, terconazole, saperconazole, troconazole, fluconazole, econazole, nystatin, amphotericin B.

Antivirals (anti-HIV, anti-Herpes) with spermicide properties: nonoxynol-9, octoxynol-9, menfegol.

Local anaesthetics: tetracaine, mepivacaine, lidocaine, benzocaine, procaine.

Anti-inflammatory Corticosteroids (glucocorticoids): beta-metasone, hydrocortisone, triamcinolone, mometasone.

Non-steroidal anti-inflammatory drugs: diclofenac, etodolac, ibuprofen, indomethacin, meloxicam, piroxicam.

Smooth muscle relaxants (β-adrenergic agonists): terbutaline, ritodrine, isoxsuprine, fenoterol, salambutol, hexoprenaline, metaproterenol, bitolterol and pirbuterol.

Labour inducers (Prostaglandins and analogues): PGE2 (dinoprostone), PGF2α (dinoprost), carboprost, sulprostone, misoprostol, gemeprost.

An especially preferred embodiment of the present invention relates to bioadhesive formulations which comprise natural micronized progesterone between 10 and 50% by weight of the formulation. These compositions are useful in treatments of luteum phase deficiencies, in particular in in vitro fertilization processes (IVF).

Another especially preferred embodiment relates to mucoadhesive formulations which contain estriol in a quantity between 0.001 and 1% by weight of the formulation. These compositions are useful in the treatment or prevention of urogenital atrophy due to estrogen deficit.

Another especially preferred embodiment relates to bioadhesive formulations which comprise clotrimazole between 1 and 50% by weight of the formulation. These compositions are useful in the treatment or prevention of vaginal candidiasis.

Another especially preferred embodiment relates to mucoadhesive formulations which contain clindamycin between 1 and 30% by weight of the formulation. These compositions are useful in the treatment or prevention of vaginosis by infection agents.

The mucoadhesive compositions of the invention may be applied in a sufficient quantity to form a layer over the entire vaginal surface, usually between 1 and 5 grams, which permits obtaining a relatively effective, safe dosage regime.

The devices that can be used with this purpose are any of those known within the state of the art, e.g. an applicator with plunger.

One of the processes that can be used to prepare the mucoadhesive formulations of the present invention comprise the steps of:

1—dissolving the preservatives in distilled water, adding, if necessary, an acidifying agent until obtaining a suitable pH so the polymers do not gel in the following step (approximately between 2.5 and 3.5), 2—adding the gelling polymers to the solution of the previous step, vigorously stirring until achieving perfect dispersion, 3—adding the neutralizing agent to the mixture of the previous step, stirring it until attaining the suitable pH for polymer gelling and for vaginal application (approximately between 4 and 5), 4—incorporating the other components of the formulation to the gel resulting from the previous step.

Alternatively, and particularly in the case of water-soluble active agents, the other components may be incorporated before forming the gel.

Furthermore, the fat-soluble active ingredients may be dissolved or dispersed in the hydrating/wetting agent before being incorporated in the gel.

Another method that may be used to obtain the mucoadhesive formulations of the present invention comprises the steps of:

1'—dissolving the preservatives in distilled water, adding an acidifying agent until obtaining a suitable pH so the polymers do not gel in the following step, 2'—adding the gelling polymers to the solution of the previous step, vigorously stirring until achieving perfect dispersion, 3'—incorporating the active ingredient to the mixture formed from the fat/lipophilic component and the solubilizing/emulsifying agent, 4'—adding the mixture of step 2' to the dispersion of step 1', 5'—adding the neutralizing agent until achieving the suitable pH for polymer gelling and vaginal application.

Without prejudice to the aforementioned, any other method of those known by a person skilled on the art may be used to prepare the formulations of the present invention.

Assays

The properties of the formulations of the present invention are revealed through the following non-limitative in vitro and in vivo assays:

1—In Vitro Bioadhesion Assays

The apparatus used to measure this property is a texture analyser, such as the TA-XT 2I texture analyser from Stable Micro Systems, U.K., and the method is that described by Peh, K. et al. in J. Pharm. Sci. 2, 1999 with certain modifications described below.

A tanned leather membrane, slightly dampened with distilled water, is placed in the unit's mobile upper support. The necessary quantity of gel to form a disc of around 4 cm diameter is deposited in the lower platform of the texture analyser.

The membrane is displaced downwards until it comes into contact with the gel and a predetermined force is applied (0.1 kg for 30 sec). Next, the separation is initiated, displacing the membrane upwards at a predetermined velocity (1 mm/s).

To evaluate the mucoadhesion of the different formulations the adhesion force and adhesion work are determined. The measurement corresponding to the adhesion force is obtained when the gel completely separates from the membrane. The adhesion work is calculated from the area under the curve obtained when representing the force which opposes the gel to the separation against time. Each gel was analysed in quintuplicate.

Using the aforementioned method (at a temperature of 25° C.) the bioadhesion of formulations A to H, was determined, defined below.

Formulation A:

| | |
|---|---|
| Clotrimazole | 25% (w/w) |
| Carbopol 971P | 0.5% |
| Polycarbophil AA-1 | 1.5% |
| Glycerine | 10% |
| NaOH | qs pH 4.5 |
| Water | qs 100% |

Formulation B:

| | |
|---|---|
| Progesterone | 25% (w/w) |
| Carbopol 971P | 0.5% |
| Polycarbophil AA-1 | 1.5% |
| Propylene glycol | 10% |
| Cremophor | 10% |
| NaOH | qs pH 4.5 |
| Water | qs 100% |

Formulation C:

| | |
|---|---|
| Progesterone | 25% (w/w) |
| Carbopol 971P | 0.5% |
| Polycarbophil AA-1 | 1.5% |
| Propylene glycol | 10% |
| NaOH | qs pH 4.5 |
| Water | qs 100% |

Formulation D:

| | |
|---|---|
| Estriol | 0.05% (w/w) |
| Carbopol 971P | 0.5% |
| Polycarbophil AA-1 | 1.5% |
| Glycerine | 10% |
| Cremophor | 10% |
| NaOH | qs pH 4.5 |
| Water | qs 100% |

Formulation E:

| | |
|---|---|
| Estriol | 0.05% (w/w) |
| Carbopol 971P | 0.5% |
| Polycarbophil AA-1 | 1.5% |
| Glycerine | 10% |
| NaOH | qs pH 4.5 |
| Water | qs 100 |

Formulation F: Commercially available (Crinone®)

| | |
|---|---|
| Progesterone | 8% |

Formulation G:

| | |
|---|---|
| Progesterone | 8% (w/w) |
| Carbopol 971P | 0.5% |
| Polycarbophil AA-1 | 1.5% |
| Propylene glycol | 10% |
| NaOH | qs pH 4.5 |
| Water | qs 100% |

Formulation H:

| | |
|---|---|
| Progesterone | 8% (w/w) |
| Carbopol 971P | 0.5% |
| Polycarbophil AA-1 | 1.5% |
| Propylene glycol | 10% |
| Cremophor | 10% |
| NaOH | qs pH 4.5 |
| Water | qs 100% |

Figure 1:
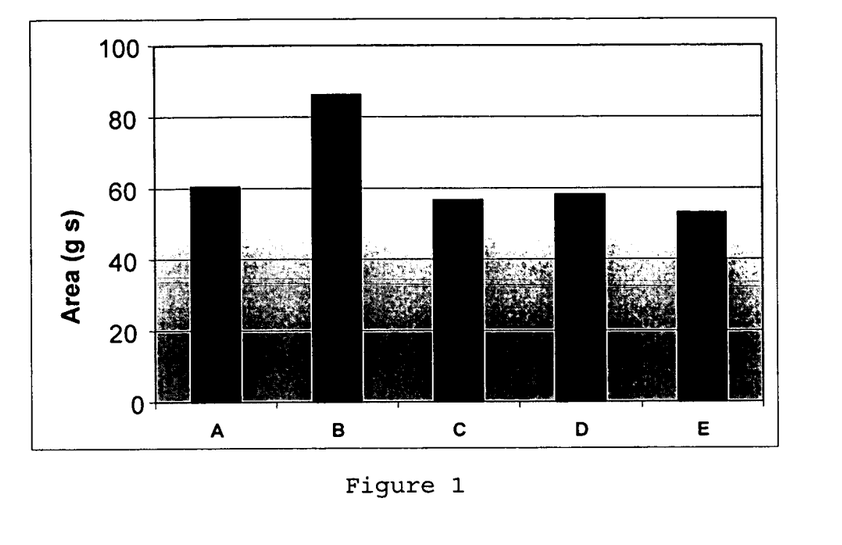
FIG. 1 graph which illustrates the in vitro bioadhesion (indicated in terms of area) of five formulations (A, B, C, D and E) in accordance with the present invention.
Figure 2:
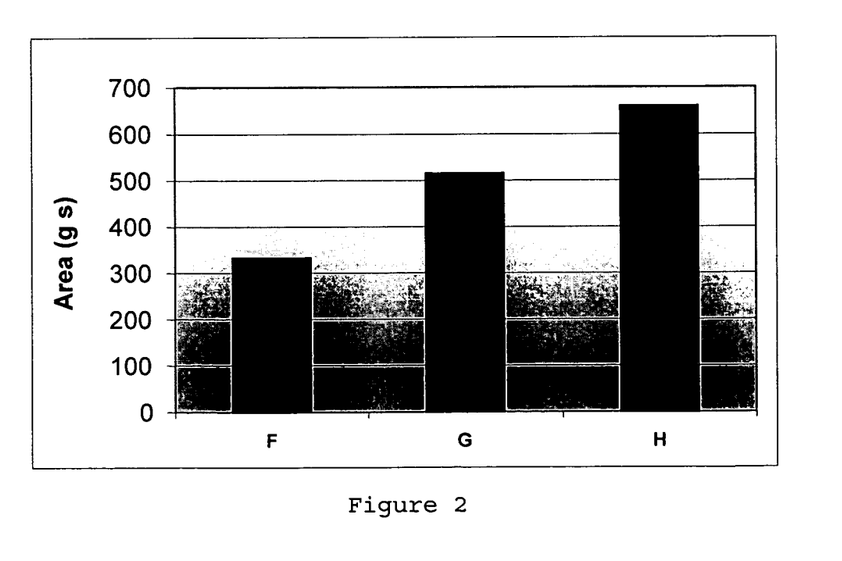
FIG. 2 graph which illustrates the compared in vitro bioadhesion of two formulations in accordance with the present invention (G and H) with a commercially available product (F).

The results obtained are shown in table I and in FIGS. 1 and 2.

TABLE I

| Formulation | Force (g) | Average area (g s) |
|---|---|---|
| A | 95,221 | 603.392 |
| B | 118.525 | 861.549 |
| C | 84,324 | 566.349 |
| D | 178.637 | 580.897 |
| E | 118,318 | 529.677 |
| F | 88.760 | 332.231 |
| G | 89.830 | 515.224 |
| H | 115.476 | 660.255 |

The analysis of these results leads to the conclusion that the gels of the present invention have excellent bioadhesive capacity, exceeding the values obtained with the commercially available formulation (Formulation F).

This characteristic is maintained even at high loads of active ingredient (Formulations A, B and C), which makes it useful in those situations where a daily application or single application of the formula is sought, as in the case of IVF treatments with progesterone and antifungal treatment with clotrimazole, respectively.

2—In Vivo Bioadhesive Assays

The present study used a total of 40 female Wistar rats, 20 ovariectomized and 20 non-ovariectomized. The 20 operated rats were randomly distributed in 4 groups with 5 animals each (groups 1A to 4A). The 20 unoperated rats were distributed in the same way (groups 1B to 4B).

The formulation of Example 5 was topically administered, using a cannula by vaginal route, at a volume of 150 µL to the 40 rats of the 8 groups. The animals can be kept for a time lightly suspended from their tails, to prevent the gel coming out.

One hour after the administration, a vaginal smear was performed on each rat of groups 1A and 1B. The same was performed after 2 hours for each rat of groups 2A and 2B, after 4 hours for rats of groups 3A and 3B, and after 6 hours for the animals of groups 4A and 4B.

Natural elimination was allowed of the gel remaining in the vaginal mucous of the 40 rats and one week later, they were all administered a volume of 150 µL of the formulation being studied.

8 hours after the administration, a vaginal smear was performed on each rat of groups 1A and 1B. 10 hours after the administration, the smear was performed on each rat of groups 2A and 2B, after 11 hours for the rats of groups 3A and 3B, and after 12 hours for the animals of groups 4A and 4B.

Again, natural elimination was allowed of the gel remaining in the vaginal mucous of all the rats and the process in the previous paragraph was repeated, in this case performing the smear after 15, 18, 21 and 24 hours for groups 1, 2, 3 and 4, respectively.

The following working scheme thus resulted:

Group 1A: ovariectomized rats, smear performed after 1, 8 and 15 hours,

Group 2A: ovariectomized rats, smear performed after 2, 10 and 18 hours,

Group 3A: ovariectomized rats, smear performed after 4, 11 and 21 hours,

Group 4A: ovariectomized rats, smear performed after 6, 12 and 24 hours,

Group 1B: non-ovariectomized rats, smear performed after 1, 8 and 15 hours,

Group 2B: non-ovariectomized rats, smear performed after 2, 10 and 18 hours,

Group 3B: non-ovariectomized rats, smear performed after 4, 11 and 21 hours,

Group 4B: non-ovariectomized rats, smear performed after 6, 12 and 24 hours.

The smears were stained with Alcian Blue and the mucoadhesion was evaluated according to the method proposed by Kockisch et. al in Journal of Controlled Release 77, 1-6 (2001).

Figure 3:
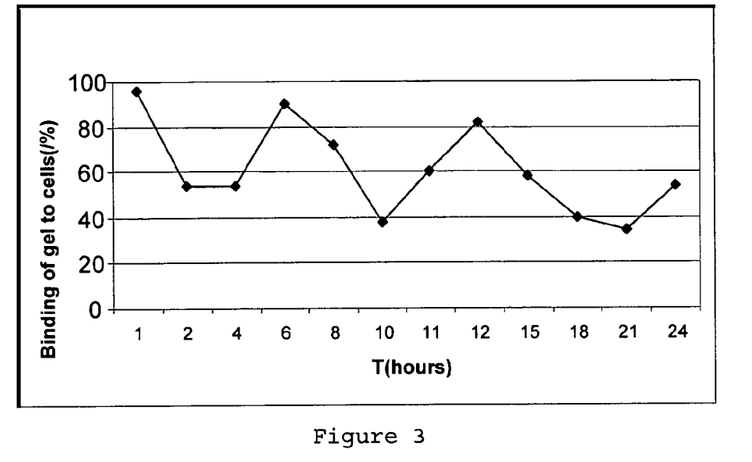
FIG. 3 graph which illustrates the in vivo bioadhesion of a 0.005% estriol formulation to the vaginal mucous of ovariectomized rats.
Figure 4:
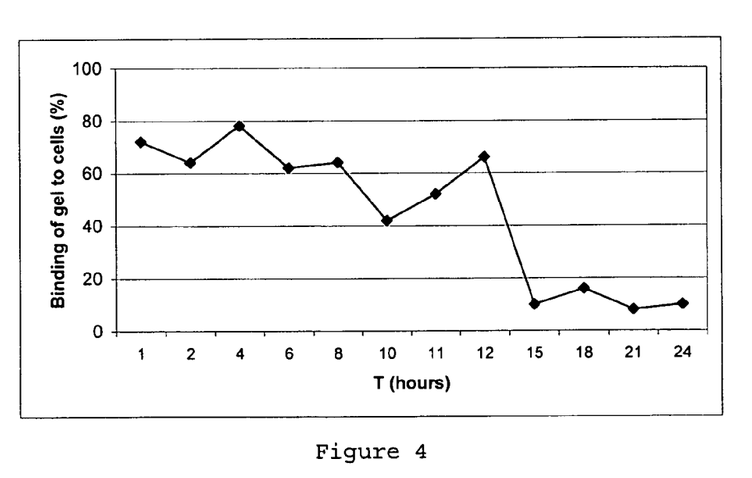
FIG. 4 graph which illustrates the in vivo bioadhesion of a 0.005% estriol formulation to the vaginal mucous of non-ovariectomized rats.

The results are shown in FIGS. 3 and 4.

The analysis of the results leads to the conclusion that the high bioadhesive capacity shown in the in vitro assays is also manifested in vivo, there still remaining gel adhered to mucous membranes 24 hours after their administration to the ovariectomized rats and after 12 hours in the unoperated rats.

3—In Vitro Transfer Assays of Estriol Formulations

The apparatus used to determine the transfer profiles is a micro dialyizer, such as the Quix Sep® by Membrane Filtration Products, Inc. USA, and the method similar to that described by Senel, S. et al. in Proceed. Int. Symp. Control. Rel. Bioact. Mater., 1998 or Chang, J.Y. et al. in Int. J. Pharm., 2002 with certain modifications described below.

Approximately 1 g of gel is deposited in the micro dialyizer device and it is covered with a Cellu Sep® T2 membrane, of 6,000-8,000 Dam, molecular cutoff size.

The system is introduced in a vessel with 25-50 ml of buffer solution and it is maintained at medium magnetic stirring.

1 ml of the solution medium is taken at the pre-established times, and it is replaced with fresh solution.

The samples obtained are quantified by spectrofluorimetry ($\chi_{excitation}$=280 nm, $\chi_{emission}$=312 nm).

A calibration line was prepared with fluorescence values for standard solutions (0.05-10 µg/ml) and it is used to obtain the estriol concentration of the different samples.

The transfer profiles of formulations J to R, defined below, are determined using the aforementioned method.

Formulation J:

| Estriol | 0.05% (w/w) |
|---|---|
| Carbopol 971P | 0.5% |
| Polycarbophil AA-1 | 1.0% |
| Propylene glycol | 10% |
| NaOH | qs pH 4.5 |
| Water | qs 100 |

Formulation K:

| Estriol | 0.05% (w/w) |
|---|---|
| Carbopol 971P | 0.5% |
| Polycarbophil AA-1 | 1.5% |
| Glycerine | 10% |
| NaOH | qs pH 4.5 |
| Water | qs 100 |

Formulation L:
The same as Form. K but it also contains 10% Cremophor.
Formulation M:
The same as Form. K but it also contains 5% Paraffin.
Formulation N:
The same as Form. K but with 10% Propylene glycol instead of 10% Glycerine
Formulation O:
The same as Form. K but it also contains 5% Labrafil.
Formulation P:
The same as Form. K but it also contains 5% Vaseline.
Formulation Q:

| Estriol | 0.005% (w/w) |
|---|---|
| Carbopol 971P | 0.5% |
| Polycarbophil AA-1 | 1.0% |
| Glycerine | 10% |
| NaOH | qs pH 4.5 |
| Water | qs 100 |

Figure 5:
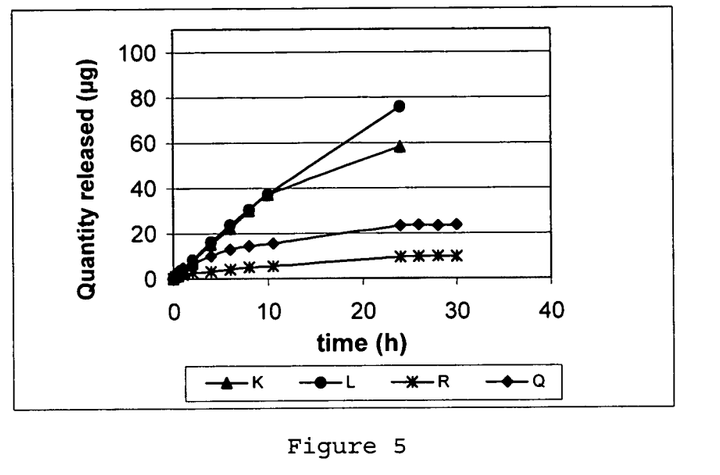
FIG. 5 graph which illustrates the in vitro transfer profiles of four formulations (K, L, Q, R) in accordance with the present invention.
Figure 6:
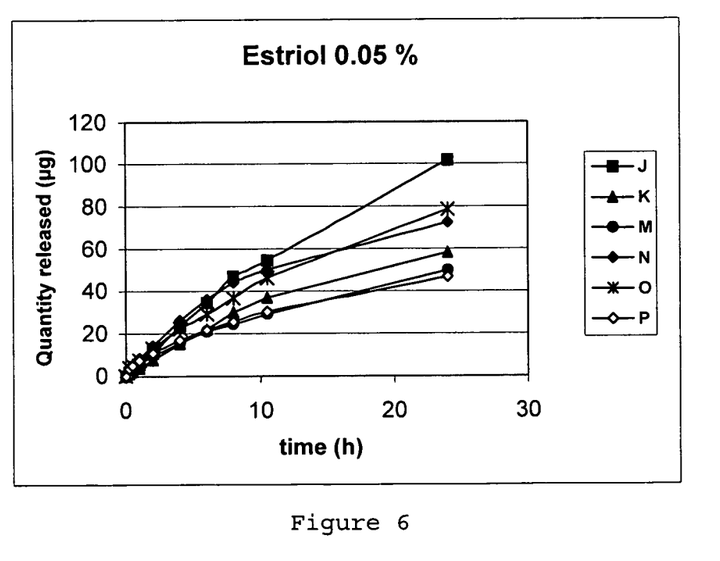
FIG. 6 graph which illustrates the in vitro transfer profiles of six formulations of 0.05% estriol with different excipients (J, K, M, N, O, P).

Formulation R:
The same as Form. Q but it also contains 10% Cremophor.
The results obtained are shown in FIGS. 5 and 6.

Their analysis leads to the conclusion that the qualitative and quantitative selection of the polymers and other excipients lets us obtain different transfer profiles of active ingredient, in accordance with the objectives sought in each case.

This characteristic is particularly important in those gels which contain drugs with dose-dependent side effects, such as the case of estrogens.

4—In Vivo Transfer and Efficacy Tests of Estriol Formulations

The present study used a total of 32 ovariectomized Wistar Han female rats which were randomly distributed in 4 groups with 8 animals each (2 animals/cage):
Group 1: treated with Formulation T (0.125 mg estriol)
Group 2: treated with Formulation E (0.125 mg estriol)
Group 3: treated with Formulation Q (0.0125 mg estriol)
Group 4: treated with Formulation S (0.005 mg estriol)
Formulation E: detailed above.
Formulation Q: detailed above.
Formulation S: the same as Formulations E and Q but containing 0.002% of estriol instead of 0.05% and 0.005% of estriol, respectively.
Formulation T: commercially available (Ovestinon®) containing 0.1% of estriol.

The pharmaceutical formulations were topically administered, by a cannula by vaginal route, at a volume of 125 μL for the first formulation and 250 μL for the three remaining formulations.

15 days after the ovariectomy, a daily vaginal smear was performed on each rat until verifying the menopausal state on all rats, determining the absence of cornified cells.

The same day that no cornified cells were detected, a sample of 0.1 mL of blood was extracted from each rat to determine the basal levels of estriol by enzymatic immunoassay (EIA) (Oxford Biomedical Commercial Kit).

The next day, the 4 formulations were administered to the 4 experimental groups and samples of 0.25 mL of blood were taken after 30 minutes and after 1, 2, 4, 6, 8, 24 and 48 hours.

The first vaginal smear was performed coinciding with the last sampling (48 h). Daily vaginal smears continued to be made until the appearance of cornified cells and then they were stopped being performed.

Determination of Estriol Plasma Levels

The blood samples were centrifuged at 12000 rpm for 2 minutes to obtain plasma which was frozen at −20° C. Once the last blood sample had been extracted (48 h), estriol was extracted from the plasma samples and it was immediately determined by EIA.

The results obtained are shown in the table II.

TABLE II

| | Estriol plasma levels (ng/ml) | | | |
|---|---|---|---|---|
| Time | Form. T | Form. E | Form. Q | Form. S |
| Basal | 0.152 | 0.144 | 0.131 | 0.109 |
| 30 minutes | 1.405 | 7.665 | 0.854 | 0.635 |
| 1 hour | 1.680 | 5.035 | 4.106 | 0.857 |
| 2 hours | 0.684 | 0.970 | 0.666 | 0.289 |
| 4 hours | 0.846 | 0.648 | 0.283 | 0.264 |
| 6 hours | 0.932 | 1.932 | 0.837 | 0.426 |
| 8 hours | 0.304 | 0.661 | 0.335 | 0.433 |
| 24 hours | 0.333 | 0.390 | 0.221 | 0.224 |
| 48 hours | 0.250 | 0.285 | 0.266 | 0.267 |

Determination of Estrogen Activity

Via the vulva, 1 mL of sterile saline solution was introduced in the rats' vagina and the exudate extraction was carefully performed. Then the smear was extended. Two smears were performed for each rat, which were fixed and stained, one using the Diff-Quick method and another with the Papanicolau method.

The effect of the treatment with each one of the formulations was observed in accordance with the appearance of cornified vaginal epithelium, according to the Allen-Doisy test. This is an estrogen activity test. The disappearance of leukocytes and the appearance of cornified cells in the vaginal smear constitutes a positive result.

The results obtained are shown in the table III.

TABLE III

| | No. of rats with presence of cornified cells Day | | | | | |
|---|---|---|---|---|---|---|
| | 0 | 2 | 3 | 4 | 5 | 6 |
| Form. T | 0/8 | 8/8 | — | — | — | — |
| Form. E | 0/8 | 8/8 | 8/8 | — | — | — |
| Form. Q | 0/8 | 7/8 | 7/8 | 7/8 | 7/8 | 7/8 |
| Form. S | 0/8 | 7/8 | 8/8 | — | — | — |

The analysis of the results obtained lead to the conclusion that the formulations of the present invention (E, Q, S), despite having concentrations between 2 and 50 times less, show a therapeutic efficacy similar to that of the commercially available formulation (Formulation T).

EXAMPLES

The invention is illustrated with the following non-limitative examples:

1—0.002% Estriol Gel Preparation Process

In a tank of suitable capacity, incorporate 2 kg of glycerine and 0.4 g of estriol. Stir at 300 r.p.m. until it is completely dissolved (approximately 12 h).

In another tank of suitable capacity, provided with a turbo-type stirring system, load 17.2 kg of demineralised water and slowly add, with constant stirring at 900 r.p.m., 36.63 g of sodium methylparaben (equivalent to 32 g of methylparaben) and 4.49 g of sodium propylparaben (equivalent to 4 g of propylparaben). It is then acidulated with HCl 37% (q.s. pH=3.0-3.5).

Stir at 500 r.p.m. for 5 minutes. Add slowly, with stirring, 300 g of Polycarbophil and 100 g of Carbopol 971P. When the incorporation has concluded, maintain the stirring at 900 r.p.m. for 30 minutes, until a perfect mixture is achieved.

The tank is covered and the previous phase is left to rest for 2 hours to achieve perfect wetting of the gelling agents.

The estriol solution in glycerine is added to the dispersion obtained with the gelling agents, with the turbo-stirrer connected. Stir for 20 minutes.

A 10% sodium hydroxide solution is added slowly to the dispersion obtained in the previous step with continuous stirring. The stirring is maintained for 15 minutes.

If it is necessary to adjust the pH of the resulting gel with 10% NaOH or 10% HCl al 10% to obtain a final pH value between 4.5 and 5.5. The weight is adjusted with demineralised water and mixed well. The gel is de-aired in a vacuum (0.8 bar) for 2 hours.

2—Progesterone Formulation

| Progesterone | 25% (w/w) |
|---|---|
| Carbopol 971P | 0.25% |
| Polycarbophil AA-1 | 0.75% |
| Propylene glycol | 10% |
| Cremophor | 10% |
| Methylparaben | 0.15% |
| Propylparaben | 0.05% |
| HCl 37% | qs pH 2.5-3.5 |
| KOH 10% | qs pH 4.5 |
| Water | qs 100% |

3—Progesterone Formulation

| Progesterone | 25% (w/w) |
|---|---|
| Carbopol 971P | 0.25% |
| Polycarbophil AA-1 | 0.75% |
| Soya lecithin | 0.4% |
| Labrafil | 37.5% |
| Methylparaben | 0.16% |
| Propylparaben | 0.02% |
| HCl 37% | qs pH 2.5-3.5 |
| NaOH 10% | qs pH 4.5 |
| Water | qs 100% |

4—Progesterone Formulation

| Progesterone | 12.5% (w/w) |
|---|---|
| Carbopol 971P | 0.25% |
| Polycarbophil AA-1 | 0.75% |
| Soya lecithin | 0.4% |
| Labrafil | 25% |
| Methylparaben | 0.16% |
| Propylparaben | 0.02% |
| HCl 37% | qs pH 2.5-3.5 |
| NaOH 10% | qs pH 4.5 |
| Water | qs 100% |

5—Progesterone Formulation

| Progesterone | 15% (w/w) |
|---|---|
| Carbopol 971P | 0.25% |
| Polycarbophil AA-1 | 0.75% |
| Polysorbate 60 | 8% |
| Labrafil | 45% |
| Methylparaben | 0.16% |
| Propylparaben | 0.02% |
| HCl 37% | qs pH 2.5-3.5 |
| NaOH 10% | qs pH 4.5 |
| Water | qs 100% |

6—Progesterone Formulation

| Progesterone | 20% (w/w) |
|---|---|
| Carbopol 971P | 0.25% |
| Polycarbophil AA-1 | 0.75% |
| Polysorbate 80 | 10% |
| Peanut oil | 50% |
| Methylparaben | 0.16% |
| Propylparaben | 0.02% |
| HCl 37% | qs pH 2.5-3.5 |
| NaOH 10% | qs pH 4.5 |
| Water | qs 100% |

7—Estriol Formulation

| Estriol | 0.05% (w/w) |
|---|---|
| Carbopol 971P | 0.5% |
| Polycarbophil AA-1 | 1.5% |
| Glycerine | 10% |
| Methylparaben | 0.15% |
| Propylparaben | 0.05% |
| HCl 37% | qs pH 2.5-3.5 |
| KOH 10% | qs pH 4.5 |
| Water | qs 100% |

8—Estriol Formulation

| Estriol | 0.005% (w/w) |
|---|---|
| Carbopol 971P | 0.5% |
| Polycarbophil AA-1 | 1.5% |
| Glycerine | 10% |
| Methylparaben | 0.16% |
| Propylparaben | 0.02% |
| HCl 37% | qs pH 2.5-3.5 |
| NaOH 10% | qs pH 4.5 |
| Water | qs 100% |

9—Clotrimazole Formulation

| | |
|---|---|
| Clotrimazole | 25% (w/w) |
| Carbopol 971P | 0.25% |
| Polycarbophil AA-1 | 0.75% |
| Glycerine | 10% |
| Cremophor | 10% |
| Methylparaben | 0.16% |
| Propylparaben | 0.02% |
| HCl 37% | qs pH 2.5-3.5 |
| KOH 10% | qs pH 4.5 |
| Water | qs 100% |

10—Clotrimazole Formulation

| | |
|---|---|
| Clotrimazole | 25% (w/w) |
| Carbopol 971P | 0.25% |
| Polycarbophil AA-1 | 0.75% |
| Soya lecithin | 0.4% |
| Labrafil | 37.5% |
| Methylparaben | 0.16% |
| Propylparaben | 0.02% |
| HCl 37% | qs pH 2.5-3.5 |
| NaOH 10% | qs pH 4.5 |
| Water | qs 100% |

11—Clindamycin Formulation

| | |
|---|---|
| Clindamycin | 10% (w/w) |
| Carbopol 971P | 0.25% |
| Polycarbophil AA-1 | 0.75% |
| Propylene glycol | 10% |
| Methylparaben | 0.16% |
| Propylparaben | 0.05% |
| HCl 37% | qs pH 2.5-3.5 |
| NaOH 10% | qs pH 4.5 |
| Water | qs 100% |

The invention claimed is:

1. A vaginal semisolid mucoadhesive formulation to treat estrogen deficit, the formulation comprising:
    a first bioadhesive gelling polymer that is a polyacrylic acid crosslinked with divinyl glycol in a quantity between 0.1% and 5% by weight of the vaginal semisolid mucoadhesive formulation;
    a second bioadhesive gelling polymer that is a polyacrylic acid crosslinked with allyl sucrose or allyl pentaerythritol in a quantity between 0.1% and 5% by weight of the vaginal semisolid mucoadhesive formulation;
    a neutralizing agent in sufficient quantity to position the vaginal semisolid mucoadhesive formulation's pH between 2 and 6;
    estriol in a quantity between 0.001% and 0.05% by weight of the vaginal semisolid mucoadhesive formulation, wherein the estriol is the only form of estrogen present in the vaginal semisolid mucoadhesive formulation; and
    water.

2. The vaginal semisolid mucoadhesive formulation of claim 1 wherein the neutralizing agent is selected from the group consisting of aqueous solutions of NaOH, KOH, and triethanolamine.

3. The vaginal semisolid mucoadhesive formulation of claim 1 further comprising at least one hydrating/wetting agent in a quantity up to 20% by weight of the vaginal semisolid mucoadhesive formulation.

4. The vaginal semisolid mucoadhesive formulation of claim 3 wherein the hydrating/wetting agent is selected from the group consisting of glycerine, propylene glycol, dipropylene glycol, polyethylene glycols, polyglycerols, sorbitol, pentaerythritol and methyl glucose ether derivatives.

5. The vaginal semisolid mucoadhesive formulation of claim 1 further comprising at least one fat/lipophilic component in a quantity up to 50% by weight of the vaginal semisolid mucoadhesive formulation.

6. The vaginal semisolid mucoadhesive formulation of claim 5 wherein the fat/lipophilic component is selected from the group consisting of paraffin, petroleum jelly, mineral oil, vegetable oils and hydrogenated vegetable oils.

7. The vaginal semisolid mucoadhesive formulation of claim 1 further comprising at least one solubilizing/emulsifying agent in a quantity up to 70% by weight of the vaginal semisolid mucoadhesive formulation.

8. The vaginal semisolid mucoadhesive formulation of claim 7 wherein the solubilizing/emulsifying agent is selected from the group consisting of fatty acid esters of polyethylene glycol, polyoxyethelenated derivatives of castor oil, phospholipids and their mixtures, fatty acids of polyoxyethylene sorbitan, sodium alkyl sulphates, sorbitan esters, glyceryl monostearate, polyoxyethylene alkyl ethers, and polyoxyethylene stearates.

9. The vaginal semisolid mucoadhesive formulation of claim 1 further comprising a preservative agent selected from the group consisting of parabens and their salts, benzoic acid and its salts, and sorbic acid and its salts, in a quantity between 0.02% and 1% by weight of the vaginal semisolid mucoadhesive formulation.

10. A process for the preparation of a vaginal semisolid mucoadhesive formulation, the process comprising:
    (a) dispersing a first bioadhesive gelling polymer that is a polyacrylic acid crosslinked with divinyl glycol in a quantity between 0.1% and 5% by weight of the vaginal semisolid mucoadhesive formulation, and a second bioadhesive gelling polymer that is a polyacrylic acid crosslinked with allyl sucrose or allyl pentaerythritol in a quantity between 0.1% and 5% by weight of the vaginal semisolid mucoadhesive formulation in a solution that comprises water and has a pH that prevents gelling of the first and second bioadhesive gelling polymers to form a mixture;
    (b) adding a neutralizing agent to the mixture to adjust to the pH of the mixture to between 2 and 6 so that it is suitable for gelling the first and second bioadhesive gelling polymers, thereby transforming the mixture into a gel; and
    (c) adding estriol in a quantity between 0.001% and 0.05% by weight of the vaginal semisolid mucoadhesive formulation to the solution, the mixture, the gel, or a combination thereof to form the vaginal semisolid mucoadhesive formulation, wherein the estriol is the only form of estrogen present in the vaginal semisolid mucoadhesive formulation.

11. The process of claim 10 wherein the solution has a pH that is approximately between 2.5 and 3.5, and the gel has a pH that is approximately between 4 and 5.

12. The process of claim 10 wherein the solution further comprises a preservative agent.

13. The process of claim 10 wherein the solution further comprises an acidifying agent.

14. The process of claim 10 wherein the estriol is dissolved or dispersed in a hydrating/wetting agent before performing step (c).

15. The process of claim 10 wherein estriol is dissolved or dispersed in a combination of a fat/lipophilic component and a solubilizing/emulsifying agent before performing step (c).

16. A method of administering estriol to a subject, the method comprising applying to one or more vaginal mucous membranes of the subject a vaginal semisolid mucoadhesive formulation that comprises:
- a first bioadhesive gelling polymer that is a polyacrylic acid crosslinked with divinyl glycol in a quantity between 0.1% and 5% by weight of the vaginal semisolid mucoadhesive formulation;
- a second bioadhesive gelling polymer that is a polyacrylic acid crosslinked with allyl sucrose or allyl pentaerythritol in a quantity between 0.1% and 5% by weight of the vaginal semisolid mucoadhesive formulation;
- a neutralizing agent in sufficient quantity to position the vaginal semisolid mucoadhesive formulation's pH between 2 and 6;
- the estriol in a quantity between 0.001% and 0.05% by weight of the vaginal semisolid mucoadhesive formulation, wherein the estriol is the only form of estrogen present in the vaginal semisolid mucoadhesive formulation; and water;

thereby administering the estriol to the subject.

17. The vaginal semisolid mucoadhesive formulation of claim 1, wherein the estriol is in a quantity between 0.001% and 0.005% by weight of the vaginal semisolid mucoadhesive formulation.

18. The vaginal semisolid mucoadhesive formulation of claim 1, wherein the estriol is in a quantity between 0.002% and 0.005% by weight of the vaginal semisolid mucoadhesive formulation.

19. The process of claim 10, wherein the estriol is in a quantity between 0.001% and 0.005% by weight of the vaginal semisolid mucoadhesive formulation.

20. The process of claim 10, wherein the estriol is in a quantity between 0.002% and 0.005% by weight of the vaginal semisolid mucoadhesive formulation.

21. The method of claim 16, wherein the estriol is in a quantity between 0.001% and 0.005% by weight of the vaginal semisolid mucoadhesive formulation.

22. The method of claim 16, wherein the estriol is in a quantity between 0.002% and 0.005% by weight of the vaginal semisolid mucoadhesive formulation.

\* \* \* \* \*

UNITED STATES PATENT AND TRADEMARK OFFICE
CERTIFICATE OF CORRECTION

| | | |
|---|---|---|
| PATENT NO. | : 8,663,688 B2 | Page 1 of 1 |
| APPLICATION NO. | : 10/565062 | |
| DATED | : March 4, 2014 | |
| INVENTOR(S) | : Acebrón Fernández et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1922 days.

Signed and Sealed this
Thirtieth Day of December, 2014

Michelle K. Lee
*Deputy Director of the United States Patent and Trademark Office*